United States Patent
Suzuki et al.

(10) Patent No.: US 8,035,185 B2
(45) Date of Patent: Oct. 11, 2011

(54) ELECTRODE, METHOD OF MAKING SAME, PHOTOELECTRIC TRANSFER ELEMENT, METHOD OF MANUFACTURING SAME, ELECTRONIC DEVICE AND METHOD OF MANUFACTURING SAME

(75) Inventors: Yusuke Suzuki, Miyagi (JP); Masahiro Morooka, Kanagawa (JP); Kazuhiro Noda, Kanagawa (JP)

(73) Assignee: Sony Corporation, Tokyo (JP)

( * ) Notice: Subject to any disclaimer, the term of this patent is extended or adjusted under 35 U.S.C. 154(b) by 854 days.

(21) Appl. No.: 10/523,483

(22) PCT Filed: May 26, 2004

(86) PCT No.: PCT/JP2004/007559
§ 371 (c)(1),
(2), (4) Date: Nov. 10, 2005

(87) PCT Pub. No.: WO2004/109840
PCT Pub. Date: Dec. 16, 2004

(65) Prior Publication Data
US 2007/0125418 A1    Jun. 7, 2007

(30) Foreign Application Priority Data
Jun. 6, 2003    (JP) .................................. 2003-161767

(51) Int. Cl.
*H01L 31/102*    (2006.01)
(52) U.S. Cl. ........................................ 257/453; 429/209
(58) Field of Classification Search ............... 257/453
See application file for complete search history.

(56) References Cited

U.S. PATENT DOCUMENTS

| | | | |
|---|---|---|---|
| 4,804,597 A | | 2/1989 | Tahara et al. |
| 5,096,663 A | * | 3/1992 | Tatarchuk .................. 419/11 |
| 5,432,023 A | * | 7/1995 | Yamada et al. .............. 429/34 |
| 5,800,631 A | * | 9/1998 | Yamada et al. ............. 136/251 |
| 6,475,670 B1 | * | 11/2002 | Ito ............................. 429/217 |
| 6,656,633 B2 | * | 12/2003 | Yamakawa et al. ......... 429/217 |
| 7,157,788 B2 | * | 1/2007 | Murofushi et al. ......... 257/643 |
| 7,422,922 B2 | | 9/2008 | Morooka et al. |
| 7,820,471 B2 | | 10/2010 | Ishibashi et al. |
| 2004/0067613 A1 | | 4/2004 | Murofushi et al. |
| 2004/0131934 A1 | * | 7/2004 | Sugnaux et al. ............ 429/209 |
| 2005/0016578 A1 | | 1/2005 | Enomoto et al. |
| 2005/0224112 A1 | | 10/2005 | Tokita et al. |
| 2006/0084257 A1 | | 4/2006 | Tokita et al. |
| 2006/0112988 A1 | | 6/2006 | Morooka |
| 2006/0137739 A1 | | 6/2006 | Imoto et al. |
| 2009/0078315 A1 | | 3/2009 | Suzuki et al. |

(Continued)

FOREIGN PATENT DOCUMENTS

JP    8-31444 A    2/1996

(Continued)

*Primary Examiner* — Thanh V Pham
*Assistant Examiner* — Caleb Henry
(74) *Attorney, Agent, or Firm* — Wolf, Greenfield & Sacks, P.C.

(57) ABSTRACT

An electrode is composed of a carbon carrying a metal and a binder polymer, and it is used as a counter electrode of a dye-sensitized solar cell. The metal carried by carbon is at least one kind of metal selected from the group consisting of Pt, Ru, Co, Ti, Ni, Al and Au. The carbon is needle-like carbon, fullerene, carbon nanotube, conductive carbon black, or the like, and its specific surface area is equal to or larger than 100 m$^2$/g.

11 Claims, 1 Drawing Sheet

U.S. PATENT DOCUMENTS

| | | |
|---|---|---|
| 2010/0255632 A1 | 10/2010 | Ishibashi et al. |
| 2010/0326516 A1 | 12/2010 | Morooka |

FOREIGN PATENT DOCUMENTS

| | | |
|---|---|---|
| JP | 11-54155 A | 2/1999 |
| JP | 11-329442 A | 11/1999 |
| JP | 2001-102104 A | 4/2001 |
| JP | 2002-102694 A | 4/2002 |
| JP | 2002-110181 A | 4/2002 |
| JP | 2002-208402 A | 7/2002 |
| JP | 2002-252002 A | 9/2002 |
| JP | 2002-298936 A | 10/2002 |
| JP | 2003-115302 A | 4/2003 |
| JP | 2004234988 A * | 8/2004 |

* cited by examiner

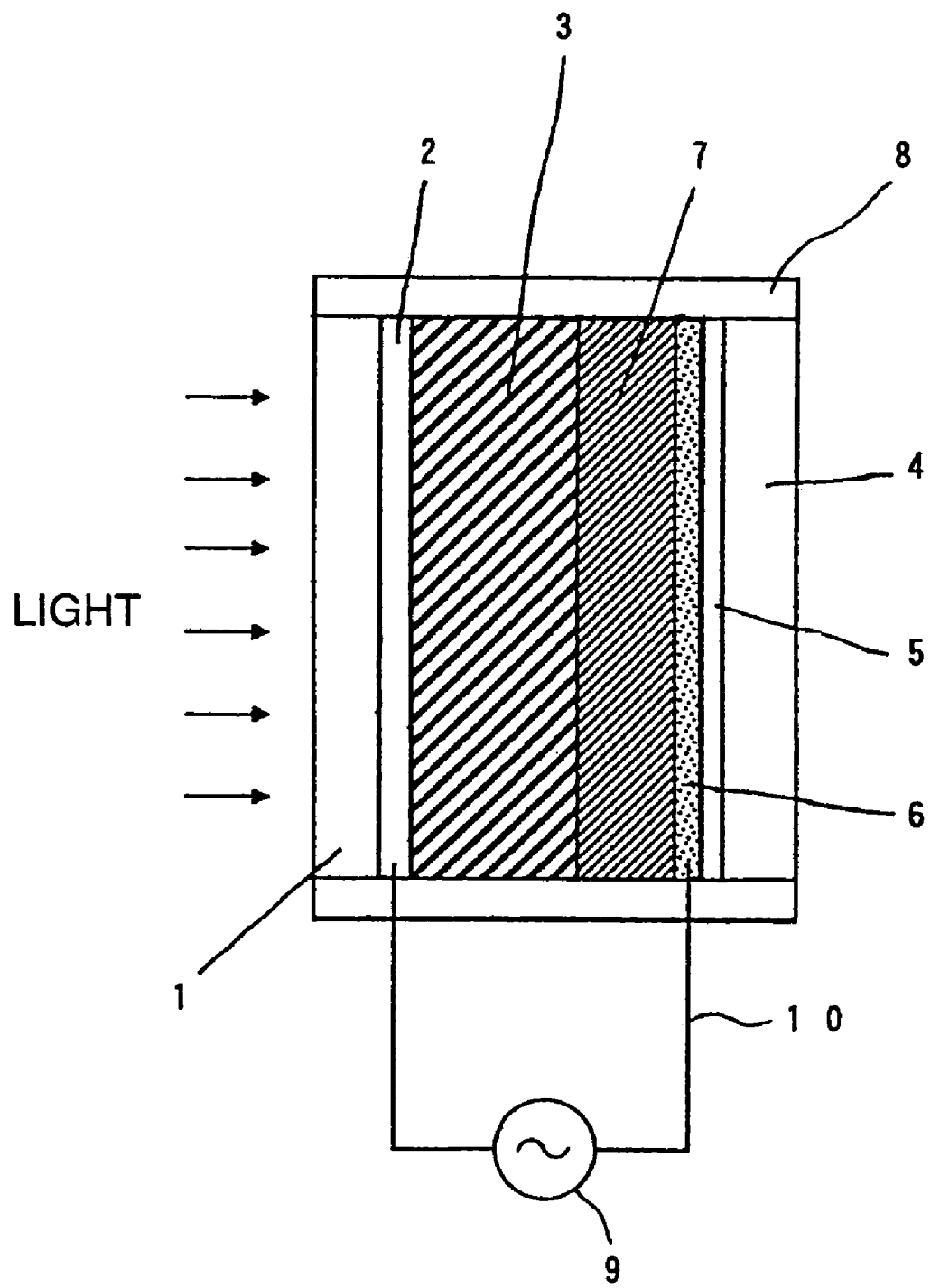

ELECTRODE, METHOD OF MAKING SAME, PHOTOELECTRIC TRANSFER ELEMENT, METHOD OF MANUFACTURING SAME, ELECTRONIC DEVICE AND METHOD OF MANUFACTURING SAME

TECHNICAL FIELD

This invention relates to an electrode, a method of forming same, a photoelectric transfer element, a method of manufacturing same, an electronic device and a method of manufacturing same, which are suitable for application to solar cells using semiconductor electrodes made of semiconductor nanoparticles.

BACKGROUND ART

Heretofore, solar cells of various materials have been examined. Among them, a number of solar cells made by using silicon have been commercially available. They are roughly classified to crystalline silicon solar cells using single crystal silicon or polycrystal silicon and amorphous silicon solar cells.

In crystalline silicon solar cells, photoelectric transfer efficiency, which is the performance of converting light (sun) energy to electrical energy, is higher than that of amorphous silicon solar cells. However, since crystalline silicon solar cells need much energy and time for crystal growth, they are disadvantageous in terms of the cost because of the low productivity.

Amorphous silicon solar cells are advantageous in higher light absorption, wider selectable range of substrates and easier enlargement of the scale. However, photoelectric transfer efficiency of amorphous silicon solar cells is lower than that of crystalline silicon solar cells. Furthermore, although amorphous silicon solar cells are higher in productivity than crystalline silicon solar cells, they need an evacuation process for the manufacture similarly to crystalline silicon solar cells and still impose a load to the manufacturing process in terms of equipment.

On the other hand, there have been long researches of solar cells using organic materials to solve the above problems. However, many of them have poor photoelectric transfer coefficient as low as 1% and have not be turned into practical use.

Among them, dye-sensitized solar cells introduced on Nature 353, 737, (1991) are remarked because they have been proved enable to realize photoelectric transfer efficiency as high as 10% and are considered manufacturable economically. The general structure of dye-sensitized solar cells is shown in, for example, Japanese Patent Laid-open Publication No. JP-H01-220380.

As counter electrodes of dye-sensitized solar cells, platinum (Pt) exhibiting small oxidation-reduction overvoltage of redox pairs has been mainly used conventionally. However, there are other reports on a method of using simplex carbon (The Electrochemical Society of Japan, Papers for 2002 Spring Symposium, Imoto et al., 3I19) and a method of using electrically conductive polymers (The Electrochemical Society of Japan, Papers for 2002 Autumn Symposium, Yanagida et al., 2E30) as well.

Iodine is known as specifically adheres onto platinum (Pt) and enabling realization of quick charge transfer (Mol. Cryst. Liq. Cryst. (1985) 121, 285)

Further known is a method of preparing $TiO_2$ paste in which titanium oxide ($TiO_2$) particles are dispersed ("Latest Technology of Dye-sensitized Solar Cells" by Hironori Arakawa, CMC, pp. 45-47 (2001))

Furthermore, a method of preparing carbon carrying Pt is known as well (Japanese Patent Laid-open Publication No. JP-H05-174838).

As referred to above, Pt has been mainly used as the counter electrode. However, charge transfer velocity on Pt electrodes is not always satisfactory. In addition, although the foregoing documents report the use of simplex carbon or electrically conductive polymers, charge transfer velocity in these methods is still insufficient.

It is therefore an object of the invention to provide an electrode higher in electron transfer velocity than Pt, simplex carbon, electrically conductive polymers, and so on, a method of manufacturing same, a photoelectric transfer element using this electrode, a method of manufacturing same, an electronic device using the same electrode and a method of manufacturing same.

DISCLOSURE OF INVENTION

The Inventor carried out various experiments and researches to solve the aforementioned problems involved in the conventional techniques, and found that the use of an electrode of a carbon carrying a metal instead of simplex carbon as the counter electrode is effective for realization of quick charge transfer on the counter electrode of a dye-sensitized solar cell. Thus, the Inventor has reached the present invention.

A method of using an electrode having high specific surface area is generally known as a method for realizing quick charger transfer. A carbon carrying a metal used in the electrode according to the invention enables realization of high charge transfer by high specific surface area as a result of using carbon and the catalytic effect of the metal carried as nanoparticles. In combination with the conventional knowledge that iodine specifically adheres onto Pt and enables realization of quick charge transfer as described in one of the above documents, realization of high charge transfer is expected especially in an electrode containing carbon of high specific surface area and Pt.

The present invention has been made through the studies mentioned above.

That is, according to the first aspect of the invention toward solution of the aforementioned problems, there is provided an electrode comprising a carbon carrying a metal and a binder.

According to the second aspect of the invention, there is provided a method of making an electrode, comprising:
forming a mixture of a carbon carrying a metal and a binder on an electrically conductive substrate.

According to the third aspect of the invention, there is provided a photoelectric transfer element using an electrode composed of a carbon carrying a metal and a binder.

According to the fourth aspect of the invention, there is provided a method of manufacturing a photoelectric transfer element, comprising the step of:
making an electrode by forming a mixture of a carbon carrying a metal and a binder on an electrically conductive substrate.

In the third and fourth aspects of the invention, the photoelectric transfer element is typically configured to place the electrode as the counter electrode in an opposed relation with a transparent electrically conductive substrate and to include a semiconductor layer and an electrolytic layer between them. The photoelectric transfer element is typically configured as dye-sensitized solar cell. However, the photoelectric transfer element may be either a solar cell other than dye-sensitized solar cell or a photoelectric transfer element other than solar cells.

Configuration of a carbon carrying a metal may be selected from various configurations. For example, the carbon may be needle-like carbon, fullerene, carbon nanotube (including a carbon nanohorn), electrically conductive carbon black (such as KETJENBLACK (trademark) or acetylene black), or the like. These various types of carbon may exhibit still better effects when they are polymerized or a functional group is introduced. Specific surface area of the carbon is preferably large to enhance the charge transfer speed on the electrode. The specific surface area of the carbon is typically at least 100 $m^2/g$, or preferably equal to or larger than 300 $m^2/g$. It is known that an electrode made by using the carbon has surface area as large as 100 times or more of the projected area. Grain size of this carbon is typically equal to or smaller than 100 nm. However, to make it easier to form the electrode, it is acceptable to mix carbon having a larger grain size. There is no specific limitation for the grain size of the carbon with the larger grain size. However, considering that the maximum thickness of the electrode is 20 to 30 μm, its maximum size will be in the order of 1 to several μm.

The metal carried by the carbon is at least one kind of metal selected from the group consisting of platinum (Pt), ruthenium (Ru), cobalt (Co), titanium (Ti), nickel (Ni), aluminum (Al) and gold (Au), for example. Candidates of the metal also include mixtures or compounds of those metals. The carbon carrying the metal assures better electrode characteristics than simplex carbon, and the electrode characteristics can be improved by increasing the amount of the carried metal. To obtain a noticeable effect of improvement of the characteristics as compared with simplex carbon, the carried metal is preferably included by the amount of at least 5 weight percent (wt %) of the carbon. In case the precious metal Pt is used as the carried metal, it is desirable to minimize its amount from the viewpoint of minimizing the cost. Thus, the amount of the metal is preferably limited not to exceed 15 wt %, for example.

In the electrode summarized above, it will be possible to use electrically conductive polymer in addition to the metal in order to enhance the favorable characteristics as the counter electrode. To form the electrically conductive polymer, various methods can be used, such as a method of casting liquid solutions of macromolecule monomers on carbon and thermally polymerizing them, a method of directly casting a polymer solution, or a method of forming it by electrolytic polymerization in a monomer solution, although they are not limitative.

In the first to fourth aspects of the invention, the electrode composed of the carbon carrying the metal and the binder is typically formed on an electrically conductive substrate. The electrically conductive substrate is typically made of glass, polymer film or metal, for example. More broadly, however, usable conductive substrates are explained below. The electrically conductive substrate may be either a simplex conductive substrate or a combination of a conductive or non-conductive support substrate and a conductive film formed on the support substrate. The conductive substrate is typically transparent. In this case, the substrate is typically an electrically conductive transparent substrate in its entirety, or may be made by forming a transparent conductive film on a conductive or non-conductive transparent support substrate. There is no specific limitation for the conductive substrate, and various materials are usable. Especially in the photoelectric transfer element, the conductive substrate preferably has high blocking capability against intruding moisture and gas from outside the photoelectric transfer element, high resistance to the solvent and high weather resistance. Examples of such substrates are transparent inorganic substrates of quartz, glass, or the like, transparent plastic substrates of polyethylene terephthalate, polyethylene naphthalate, carbonate, polystyrene, polyethylene, polypropylene, polyphenylene sulfide, polyvinylidene fluoride, tetraacetyl cellulose, phenoxy bromide, aramid, polyimide, polystyrene, polyarylate, polysulfone, polyolefin, and so forth. However, materials of the substrate are not limited to them. Taking easier workability and lighter weight into account, a transparent plastic substrate is preferably used as the conductive substrate. There is no specific limitation for the thickness of the conductive substrate. Any thickness is selectable depending upon the light transmittance, blocking capability between the inside and the outside of the photoelectric transfer element, and other factors.

The smaller the surface resistance, the better the conductive substrate. More specifically, the surface resistance of the conductive substrate is preferably 500Ω/□ or less, and more preferably 100Ω/□ or less. In case the conductive substrate is made by forming a conductive film on a support substrate, known materials can be used. Examples of such materials are indium-tin complex oxide (ITO) fluorine-doped $SnO_2$ (FTO) and $SnO_2$. They are not limitative, but two or more of them can be used in combination. For the purpose of reducing the surface resistance of the conductive substrate and thereby enhancing the collecting efficiency, a pattern of metal wiring of high conductivity can be made on the conductive substrate.

Also as the substrate on which the semiconductor layer is formed, various substrates of the materials and structures explained above can be used.

The binder for forming a complex with the carbon carrying the metal may be selected from known materials such as various kinds of pitch, rubber, plastic resin, and so on. The binder is preferably insoluble to electrolytes. More specifically, examples of materials usable as the binder include fluoroplastics such as polyvinylidene fluoride (PVDF), polytetrafluoro ethylene (PTFE), tetrafluoroethylene hexafluropropylene copolymer (FEP), tetrafluroethylene perfluoroalkylvinylether copolymer (PFA), ethylene tetrafluoroethylene copolymer (ETFE), polychlorotrifluoroethylene (PCTFE), ethylene chlorotrifluoroethylene copolymer (ECTFE), polyvinyl fluoride (PVF), etc.; vinylidene fluoride-based fluororubbers such as vinylidene fluoride hexafluoropropylene-based fluororubbers (VDF-HFP-based fluororubbers), vinyliden fluoride hexafluropropylene tetrafluroethylene-based flurororubbers (VDF-HFP-TFE-based fluororubbers), vinyliden fluoride penthafluoropropylene-based fluororubbers (VDF-PEP-based fluororubbers), vinylidene fluoride penthafluoropropylene tetrafluroethylene-based flurorubbers (VDF-PEP-TFE-based fluoro rubbers), vinylidene fluoride perfluro-methylvinylether tetrafluroethylene-based fluororubbers (VDF-PFMVE-TFE-based fluororubbers, vinylidene fluoride chlorotrifluoroethylene-based fluororubbers (VDF-CTFE-based fluororubbers), etc.; tetrafluroethylene propylene-based fluororubbers (TFE-P-based fluororubbers); tetrafluoroethylene perfluoroalkylvinylether-based flurorubbers; thermoplasitc flurorubbers (such as DAI-EL thermoplastic manufactured by Daikin Industries, Ltd.); polyethylene glycol (PEG); ethylene propylene diene monomer (EPDM); and cellulose such as carboxymethyl cellulose (CMC). Among them, polyvinylidene fluoride (PCDF) can be dissolved especially by solvent, and can be easily mixed with slurry. In addition, this is desirable because of stability to light, heat, etc. The binder may be a combination of two or more of the above-mentioned materials.

The binder is typically prepared and used by dissolving or dispersing a powdered binder material in a solvent. However, powder of a binder material may be used directly without using a solvent. There is no specific limitation for the solvent to be used, and any appropriate solvent may be selected from various kinds of solvents including water, metylethyl ketone, cyclohexanone, isophorone, N-methylpyrrolidone, N,N-dimethyl formamide, N,N-dimetyl acetamide, toluene, and so forth, depending upon the purpose.

Regarding the quantity of the solvent to be added, there is no specific limitation provided sufficient adhesive force to a base material used in a later manufacturing process or in operation is obtained. Typically, however, quantity of the binder to be added is 5 wt % or more, or more preferably 15 wt % or more of the carbon. Too little binder will result in insufficient adherence to the base material, and too much binder will result in insufficient characteristics of the electrode.

Regarding the way of forming the mixture of the carbon carrying the metal and the binder on the conductive substrate, there is not specific limitation. Any appropriate one of known methods such as metal mask printing, electrostatic coating, dip coating, spray coating, roll coating, doctor blade technique, gravure coating, screen printing, and so on, may be used. After that, rolling treatment by a flat press, calendar roll, or the like, may be added, if necessary.

In the photoelectric transfer element, the semiconductor layer formed between the transparent conductive substrate and the above-explained electrode as the counter electrode is typically composed of semiconductor nanoparticles. Usable materials of the semiconductor nanoparticles are element semiconductors represented by silicon as well as various compound semiconductors, oxide semiconductors, and so forth. These semiconductors are preferably n-type semiconductors in which electrons in the conduction band behave as carriers and provide an anode current. Examples of these semiconductors are metal oxides such as $TiO_2$, MgO, ZnO, $WO_3$, $Nb_2O_3$, $TiSrO_2$ and $SnO_2$. Among them, $TiO_2$ (especially of the anatase structure) is especially desirable. However, usable semiconductors are not limited to those examples, and any complex combining two or more of them may is also usable.

There is no specific limitation to the grain size of the semiconductor nanoparticles. However, it is preferably 1 to 200 nm and more preferably 5 to 100 nm in average grain size of primary particles. It is also possible to mix semiconductor nanoparticles having a larger average grain size with the semiconductor nanoparticles having the aforementioned average grain size to scatter incident light by the semiconductor nanoparticles having the larger average grain size scatter and thereby enhance the quantum yield. In this case, the average grain size of the semiconductor nanoparticles added is preferably 20 to 500 nm.

The sensitizing dye carried by the semiconductor nanoparticles may be selected freely provide it brings about a sensitizing function. Examples of usable dyes include xanthene-based dyes such as bipyridine, phenanthrene derivatives, rhodamine B, rose bengal, eosin and Erythrocin; cyanine-based dyes such as quinocyanine and cryptocyanine; basic dyes such as phenosafranine, Capri blue, thiocin and methylene blue; porphyrin-based compounds such as chlorophyll, zinc porphyrin and magnesium porphyrin; azo dyes; phthalocyanine compounds; coumarin-based compounds; anthraquinone-based dyes; and polycyclic quinone-based dyes. Complex with a metal such as ruthenium (Ru), zinc (Zn), platinum (Pt) or palladium (Pd) is also usable as the sensitizing dye. In particular, Ru bipyridine complex compound is preferable because of its high quantum yield. Any mixture of two or more kinds of those substances is also usable as the sensitizing dye.

The sensitizing dye may be carried by the semiconductor nanoparticle layer in any form or manner. For example, a typical method is to dissolve the sensitizing dye in a solution such as various kinds of alcohol, various kinds of nitrile, nitromethane, halogenated hydrocarbon, various kinds of ether, dimethyl sulfoxide, various kinds of amide, N-methyl pyrrolidone, 1,3-dimethyl imidazolidinone, 3-methyl oxazolidinone, various kinds of ester, various kinds of carbonic acid ester, various kinds of ketone, hydrocarbon, water, and so on, next immerse the semiconductor nanoparticle layer therein, or coating the semiconductor nanoparticle layer with the dye solution. Also employable is a method of dissolving the sensitizing dye in a paste in which semiconductor nanoparticles are dispersed, then coating a layer with semiconductor particles previously carrying the sensitizing dye, and press-molding the layer. In this case, amount of sensitizing dye molecules absorbed by each semiconductor nanoparticle is preferably 1 to 10000 molecules, or more preferably 1 to 3000 molecules. The dye molecules may be either monomolecular or in form of association. To control the association, temperature and pressure for the carrying may be changed. To reduce association of sensitizing dye molecules themselves, a kind of carboxylic acid such as deoxycholic acid may be added. An ultraviolet absorber may be additionally used as well.

The electrolytic layer contains at least one kind of substances reversibly changeable in state between oxidation and reduction (redox system, which is dissolved in an electrolyte. Examples of the redox system are halogen system such as I—/$I_3$— and Br—/$Br_2$, quasi-halogen system such as quinone/hydroquinone and SCN—/$(SCN)_2$, iron (II) ion/iron (III) ion, copper (I) ion/copper (II) ion, and so on, although not limitative to them.

The electrolyte may be a liquid electrolyte. Alternatively, the electrolyte may be prepared in form of a gel electrolyte, polymeric solid electrolyte, inorganic solid electrolyte, or the like, which contains a liquid electrolyte in a polymeric substance. More specifically, the electrolyte may be a combination of iodine ($I_2$) and a metal iodide or an organic iodide, a combination of bromine ($Br_2$) and a metal bromide or an organic bromide, a metal complex such as ferrocyanide/ferricinium ion, a sulfur compound such as sodium polysulfide or alkylthiol/alkyl disulfide, viologen dye, hydroquinone/quinone, or the like. Preferable cations of the above-mentioned metal compounds are Li, Na, K, Mg, Ca, Cs, etc. Preferable cations of the above-mentioned organic compounds are quaternary ammonium compounds such as various kinds of tetra alkyl ammonium, various kinds of piridinium, various kinds of imidazolium, and so forth. However, the cations are not limited to these materials, but combinations of two or more kinds of them may be used. Among them, electrolytes made by combining $I_2$ with an ionic liquid such as LiI, NaI, imidazolium iodide, quaternary ammonium iodide, or the like. Concentration of the electrolyte salt is preferably 0.05M to 5M, or more preferably 0.2M to 1M. Concentration of $I_2$ and $Br_2$ is preferably 0.0005M to 1M, or more preferably 0.001M to 0.1M. To enhance the release voltage, various kinds of additives such as 4-tert-butyl pyridine or carboxylic acid may be added.

Usable as the solvent of the electrolyte are, for example, the nitrile system including acetonitrile, carbonate system including propylene carbonate and ethylene carbonate, gamma butyrolactone, pyridine, dimethyl acetamide, other polar solvents, cold-melting salts such as methyl propyl imidazolium-iodine, and their mixtures. Commoner solvents of the electrolyte are water, various kinds of alcohol, ether, ester, ester carbonate, lactone, carboxylic ester, phosphoric triester, heterocyclic compounds, various kinds of nitrile, ketone, amide, nitromethane, halogenated hydrocarboon, dimethyl sulfoxide, sulfolane, N-methyl pyrrolidone, 1,3-dimethyl imidazolidinone, 3-methyl oxazolidinone and hydrocarbon. Mixtures of two or more of these materials are also usable. Furthermore, ionic liquids of the tetraalkyl system, pyridinium system, quaternary ammonium salt of the imidazolium system can be used as the solvent.

The electrolyte may additionally contain a supporting electrolyte where necessary. Examples of the supporting electrolyte are inorganic salts such as lithium iodide and sodium iodide, and molten salts such as imidazolium and quaternary ammonium.

The photoelectric transfer element may be made by any method. For example, the electrolytic composite can be in a liquid form or may be gelated inside the photoelectric transfer element. In case the electrolytic composite is in a liquid form before it is introduced, the semiconductor electrode and the counter electrode are opposed to each other, and the part of the substrate not covered by the semiconductor electrode is sealed such that these two electrodes do not contact. In this case, size of the gap between the semiconductor electrode and the counter electrode is normally 1 to 100 μm or more preferably 1 to 50 μm, although it is not limitative. If the distance between the electrodes is excessively long, photoelectric current will decreases due to a decrease of the electrical conductivity. The sealing may be formed by any method, but the use of a light-resistant, insulative and material reactive to light, insulative and dampproof material is preferable. Various welding methods, epoxy resin, ultraviolet-curing resin, acrylic adhesive, EVA (ethylene vinyl acetate), ionomer resin, ceramic, heat-welding film, etc. can be used. An inlet for introducing the solution of the electrolytic composite is required. Location of the inlet preferably avoids the counter electrode, although it is not limitative. The solution may be introduced by any method, but a method of introducing the solution into the cell already sealed except an inlet. In this case, it is easy to pour several drops of the solution into the inlet and introduce them into the cell by capillary phenomenon. Introduction of the solution may be conducted under a reduced pressure or a heated condition where necessary. After the required amount of the solution is fully introduced inside, an extra amount of the solution remaining in the inlet is removed, and the inlet is sealed. The inlet may be sealed by any method. If necessary, it can be sealed by bonding a glass plate or a plastic substrate with a sealing agent. In case the electrolyte is a gel electrolyte using a polymer, or the like, or a total solid electrolyte, the polymer solution containing the electrolytic composite and a plasticizer is vaporized and removed on the semiconductor electrode carrying the dye by a casting method. After the plasticizer is fully removed, the inlet may be sealed by the same method. The sealing is preferably done in an atmosphere of an inactive gas or under a reduced pressure by using a vacuum sealer, for example. After the sealing, heating and pressing may be carried out to assure sufficient impregnation of the electrolyte into the semiconductor nanoparticle layer.

The photoelectric transfer element can be made in various non-limitative forms depending upon the use.

The aforementioned electrode comprising the carbon carrying the metal and the binder, as well as the method of forming the electrode by forming the mixture of the carbon carrying the metal and the binder on the conductive substrate, is applicable not only to photoelectric transfer elements but also to all electronic devices using electrodes.

Thus, the fifth aspect of the invention is an electronic device using a carbon carrying a metal and a binder.

The sixth aspect of the invention is a method of manufacturing an electronic device comprising the step of forming an electrode by forming a mixture of a carbon carrying a metal and a binder on a conductive substrate.

The explanation and discussion made in conjunction with the first to fourth aspects of the invention are applicable to the fifth and sixth aspects of the invention provided they are consistent to their natures.

According to the invention having the above-summarized configuration, since a carbon carries a metal, the high specific surface of the carbon and catalytic action of the carried metal greatly enhance the charge transfer velocity on the electrode.

BRIEF DESCRIPTION OF DRAWINGS

FIG. 1 is a cross-sectional view of the substantial part of a dye-sensitized solar cell according to an embodiment of the invention.

BEST MODE FOR CARRYING OUT THE INVENTION

An embodiment of the invention will now be explained below with reference to the drawing.

FIG. 1 shows a dye-sensitized solar cell embodying the invention.

As shown in FIG. 1, the dye-sensitized solar cell comprises two parts opposed to each other via a predetermined distance. One of these parts comprises a transparent electrode and a metal oxide semiconductor layer 3 (semiconductor electrode) sequentially formed on a transparent substrate 1. The other parts comprises an electrode 5 and a counter electrode 6 sequentially formed on a substrate 4. In the space between those two parts, an electrolyte layer 7 is formed. The entirety is housed sealed in a case 8. Instead of being housed in the case 8, the entirety may be sealed with a resin. The transparent electrode 2 and the counter electrode 6 are connected by a conducting wire to form a current circuit 10 with an ammeter 9. In this structure, light impinges the metal oxide semiconductor layer 3 from through the transparent substrate 1.

The electrode 5 may be omitted. To enhance the adhesion between the counter electrode 6 and the electrode 5, or the adhesion between the counter electrode and the substrate 4 in case the electrode 5 is omitted, a layer of Cr or the like may be interposed between them. The electrode 5 and the counter electrode 6 may be formed integral. The electrode 5 is made of, for example, glass, transparent conductive glass, metal, polymer film, or the like, although not limitative to these examples. However, material of the electrode 5 is preferably selected from those not reacting the electrolyte layer 7 when contacting it through pinholes in the counter electrode 6, if any.

The transparent substrate 1 and the substrate 4 can be selected from examples shown above, depending upon given requirements. For example, they may be glass substrates, transparent plastic substrate, or the like.

The transparent electrode 2 is made of a transparent conductive material. More specifically, the transparent electrode 2 may be a single film of ITO most widely known as a transparent conductive material non-doped or doped with an element such as Zr, Hf, Te, F, or the like, or may be a multi-layered structure of such a film and a film of another transparent conductive material. The multi-layered structure may be made by stacking a film of a metal such as Au, Ag or Cu between ITO films, for example, although it is not limitative.

The metal oxide semiconductor layer 3 includes metal oxide semiconductor nanoparticles sintered on the transparent electrode 2, for example. Material of the metal oxide semiconductor layer 3 can be selected from the aforementioned materials, for example, depending upon given requirements.

A sensitizing dye (not shown) is carried on the metal oxide semiconductor layer 3 to sensitize it. The sensitizing dye can be selected from the aforementioned materials, for example, depending upon given requirements.

The electrolyte, redox system, solvent, etc. of the electrolyte layer 7 can be selected from the aforementioned materials, for example, depending upon give requirements. The electrolyte layer 7 may contain a supporting electrolyte, if necessary. The supporting electrolyte can be selected from the aforementioned materials, for example, depending upon give requirements.

In this case, the counter electrode 6 comprises carbon carrying a metal and binder polymer. Essentially, the carbon carrying the metal may take any form. Preferably, however, it is in form of carbon nanotubes (including carbon nanohorns), acicular carbon, KETJENBLACK (trademark), acetylene black, or the like. The metal carried by the carbon may be at least one kind of metal selected from the group consisting of Pt, Ru, Co, Ti, Ni, Al and Au. Amount of the metal carried by the carbon is 5 wt % or more, for example, relative to the carbon. The binder polymer may be selected from the aforementioned materials, for example, depending upon given requirements.

The counter electrode 6 composed of carbon carrying a metal and binder polymer can be made by the following process, for example. The following explanation is made as using Pt as the metal.

First, a carbon carrying Pt is prepared by, for example, the method described in Patent Document 2. That is, 1 g of chloroplatinic acid ($H_2PtCl_6$) is dissolved in 250 cc of distilled water, and 10.6 cc of 30 wt % hydrogen peroxide is added and stirred. After that, thiosulfuric acid $Na_2S_2O_4$ water solution 60 g/1,106 cc is added and stirred to prepare colloidal Pt. Also prepared is a carbon-dispersed solution in which 1 weight part of carbon for previously carrying colloidal Pt is well dispersed in 100 weight part of distilled water by an ultrasonic agitator. The carbon-dispersed solution, heated to 60° C., is instilled to have the carbon carry Pt catalyst. Then, it is filtered by suction filtration and cleaned well. Thus, the carbon carrying Pt is obtained.

Subsequently, binder polymer (such as N-methyl pyrrolidone (NMP) and PVDF, for example) is added to the carbon carrying Pt, and they are mixed until the mixture becomes uniform. The mixture is next coated on the electrode 5 by screen printing, blade coating, or the like; then dried by heating and/or depressurization; and pressed. Thus, the counter electrode 6 comprising the carbon carrying Pt and the binder polymer is obtained. When the mixture is pressed, heating may be additionally used. In this process, temperature is preferably controlled to be equal to or higher than the glass transition point of the binder polymer used, such as PVDF.

In case the binder is a water-soluble polymer such as cellulose or PTFE, while water and isopropanol are gradually added, the binder polymer of 50 wt % relative to carbon, for example, is mixed until the mixture becomes uniform. Then, the mixture is coated on the electrode 5 by screen printing, blade coating, or the like; then dried by heating and/or depressurization; and pressed. Thus, the counter electrode 6 comprising carbon carrying a metal and binder polymer is obtained. Here again, temperature is preferably controlled to be equal to or higher than the glass transition point of the binder polymer used, such as PVDF.

Operation mechanism of the dye-sensitized solar cell is as explained below.

Light entering through the transparent substrate 1 excites the sensitizing dye carried by the metal oxide semiconductor layer 3, and the excited sensitizing dye quickly delivers electrons to the metal oxide semiconductor layer 3. On the other hand, the sensitizing dye losing electrons receives electrons from ions of the electrolyte layer 7 that is a carrier transfer layer. Molecules having delivered electrons again receive electrons in the counter electrode 6. In this manner, a current flows between the electrodes. Since the transparent electrode 2 and the counter electrode 6 are connected by a current circuit 10 as already explained, electrons generated flow into the counter electrode 6 via the metal oxide semiconductor layer 3. As a result, electric energy can be obtained between the transparent electrode 2 and the counter electrode 6.

As explained above, according to the embodiment, since the solar cell uses the counter electrode 6 composed of carbon carrying a metal such as Pt and binder polymer, it is possible to enhance the charge transfer velocity on the counter electrode 6 by high specific surface area of the carbon and the catalytic action of Pt or other metal carried by the carbon as compared with conventional solar cells using Pt, simplex carbon or conductive polymer as the counter electrode 6. As a result, it is possible to enhance the photoelectric transfer property of the dye-sensitized solar cells.

Some examples are explained below.

Example 1

$TiO_2$ nanoparticles were used as the semiconductor nanoparticles. $TiO_2$ paste was prepared in the following manner with reference to Non-patent Document 5.

First, 125 ml of titanium isopropoxide was slowly instilled into 750 ml of 0.1 M nitric acid water solution at the room temperature while the solution is stirred. After completion of the instillation, the solution was transferred to a constant temperature bath of 80° C. and stirred for eight hours. Thus, a cloudy semitransparent sol solution was obtained. The sol solution was allowed to cool to the room temperature, then passed through a glass filter, and measured up to 700 ml. The sol solution obtained was transferred to an autoclave, then treated by hydrothermal processing at 220° C. for 12 hours and thereafter put under dispersion processing by supersonic processing for one hour. After that, the solution was concentrated by an evaporator at 40° C. to adjust the content of $TiO_2$ to 11 wt %. Then, polyethylene oxide (PEO) of molecular weight 500,000 was added to the concentrated sol solution, and they were mixed uniformly by a planet ball mill. Thus, $TiO_2$ paste increased in viscosity was obtained.

The $TiO_2$ paste was coated over the area of 0.7 cm×0.7 cm on FTO used as the transparent electrode 2 by screen printing. Thereafter, the FTO was held in a nitrogen atmosphere at 450° C. for 60 minutes, and nanoporous $TiO_2$ electrodes were sintered on the FTO substrate (sheet resistance; 15Ω/□).

After that, the FTO substrate was immersed in dehydrated ethanol solution in which 0.5 mM of cis-bis(isothiocyanate)-N,N-bis(2,2'-dipyridil-4,4'di-carbonic acid)-ruthenium(II) dihydrate and 20 mM of deoxycholic acid were dissolved for 12 hours to have it absorb the sensitizing dye. The electrode was next cleaned sequentially in ethanol solution of 4-tert-butyl pyridine and dehydrated ethanol, and thereafter dried in the dark.

The counter electrode 6 was made by the following method.

50 wt % of PVDF relative to carbon was added to carbon carrying 40 wt % of Pt. Further, NMP in the amount of 20 times in weight of carbon was slowly added, and they were mixed uniformly. The mixture was coated at intervals of 250 µm by blade coating, and dried by vacuum heating at 160° C. for 8 hours. Then, while heated and maintained at 120° C., it was pressed with the pressure of 300 kg/cm$^3$ for three minutes. Thus, the counter electrode 6 made of carbon carrying Pt and binder polymer.

Further, 2 g of lithium iodide (LiI), 5 g of 1-propyl-2,3 dimethyl imidazolium iodide, 0.5 g of iodide (I$_2$) and 2 g of 4-tert-butyl pyridine were dissolved in 30.5 g of acetonitrile to prepare the electrolytic solution.

The obtained electrolyte liquid was instilled onto the metal oxide semiconductor layer 3, and the counter electrode 6 was brought onto it via a silicon rubber spacer (30 µm thick). Thus, the due-sensitized solar cell was obtained.

Example 2

A dye-sensitized solar cell was prepared in the same manner as Example 1 by using carbon carrying 40 wt % of Pt and Ru in the ratio of 1:1 in weight, and its I-V characteristics were evaluated.

Example 3

A dye-sensitized solar cell was prepared in the same manner as Example 1 excepting that the pressing for making the counter electrode 6 was carried out at normal temperatures, and I-V characteristics of the solar battery were evaluated.

Example 4

A dye-sensitized solar cell was prepared in the same manner as Example 1 except that the counter electrode was prepared as explained below, and I-V characteristics of the solar battery were evaluated.

200 wt % of water, 300 wt % of IPA and 30 wt % of HEC (hydroxyethyl cellulose) respectively relative to carbon were added to carbon carrying 40 wt % of Pt, and they were mixed together uniformly. Then, the mixture was coated by blade coating at 250 µm intervals, and it was dried by heating at 80° C. for 8 hours. Then, while heated and maintained at 120° C., it was pressed with the pressure of 300 kg/cm$^3$ for three minutes. Thus, the counter electrode 6 made of carbon carrying Pt and binder polymer.

Example 5

A dye-sensitized solar cell was prepared in the same manner as Example 4 by using carbon carrying 40 wt % of Pt and Ru in the ratio of 1:1 in weight, and its I-V characteristics were evaluated.

Example 6

A dye-sensitized solar cell was prepared in the same manner as Example 4 excepting that the pressing for making the counter electrode 6 was carried out at normal temperatures, and I-V characteristics of the solar battery were evaluated.

Example 7

A dye-sensitized solar cell was prepared by using a gel electrolyte, and its I-V characteristics were evaluated.

Electrolytic solution was prepared by dissolving 2 g of lithium iodide (LiI), 5 g of 1-propyl-2,3 dimethyl imidazolium iodide, 0.5 g of iodide (I$_2$) and 2 g of 4-tert-butyl pyridine were dissolved in 30.5 g of gamma butyrolactone. 150 g of dimethyl carbonate was added to the electrolytic solution as a diluent, and the solution was heated to 70° C. After that, 8 g of poly(vinylidene fluoride-hexafluoropropylene) copolymer having the molecular weight of 300,000 was dissolved to obtain a sol gel electrolyte precursor. The poly(vinylidene fluoride-hexafluoropropylene) copolymer was copolymer containing vinylidene and hexafluropropylene by 95:5.

The sol gel electrolyte precursor was coated by blade coating on a metal oxide semiconductor layer 3 formed on a SnO$_2$-coated ITO and having absorbed a sensitizing dye in the same manner as Example 1. Then, it was dried at 50° C. for five minutes to remove dimethyl carbonate. Thus, the metal oxide semiconductor layer 3 with the gel electrolyte was obtained.

The metal oxide semiconductor layer 3 with the gel electrolyte was combined with the counter electrode 6 and silicone rubber spacer used in Example 1 to complete the dye-sensitized solar cell.

Comparative Example 1

A dye-sensitized solar cell was prepared in the same manner by using a 100 nm thick Pt film formed by sputtering as the counter electrode, and its I-V characteristics were evaluated.

Comparative Example 2

A dye-sensitized solar cell was prepared by making the counter electrode was prepared in the same manner as Example 1 except that the final pressing was omitted, and its I-V characteristics were evaluated.

Evaluation of I-V Characteristics

Photoelectric transfer characteristics of the individual dye-sensitized solar cells prepared as explained above.

To evaluate the photoelectric transfer efficient, alligator clips were connected to the transparent substrate 1 and the counter electrode 6 in each dye-sensitized solar cell, and the dye-sensitized solar cell was exposed to light. Then, a current generated thereby was measured by a current/voltage measuring device. For lighting, a xenon lamp was used as the light source, and the light intensity was adjusted to 100 mW/cm$^2$ on each dye-sensitized solar cell Results of the evaluation of photoelectric transfer characteristics are shown in Table 1.

TABLE 1

| Photoelectric Transfer Coefficient | |
|---|---|
| Example 1 | 6.1% |
| Example 2 | 6.0% |
| Example 3 | 5.8% |
| Example 4 | 5.9% |
| Example 5 | 5.8% |
| Example 6 | 5.9% |
| Example 7 | 6.0% |
| Comparative Example 1 | 5.6% |
| Comparative Example 2 | 5.4% |

As appreciated from Table 1, solar cells prepared in Examples 1-7 using the counter electrode 6 made of carbon carrying Pt and binder polymer exhibit relatively high photoelectric coefficients as compared with Comparative Examples 1 and 2.

Heretofore, a specific embodiment of the prevent invention has been explained. However, the invention is not limited to this embodiment, but contemplated various changed or modifications based on the technical concept of the invention.

Fog example, numerical values, structures, shapes, materials, source materials, processes, and so on, are not but mere examples, and any other appropriate numerical values, structures, shapes, materials, source materials, processes, and so on, may be employed, if necessary.

As described above, according to the invention, since the electrode comprises a carbon carrying a metal and a binder, the charge transfer velocity on the electrode is enhanced as compared in a device where the electrode is made of Pt, simplex carbon, conductive polymer, or the like. Additionally, by using this electrode as the counter electrode, for example, it is possible to enhance the photoelectric transfer characteristics of the photoelectric transfer element of a dye-sensitized solar cell, for example.

| DESCRIPTION OF REFERENCE NUMERALS | |
|---|---|
| 1 | TRANSPARENT SUBSTRATE |
| 2 | TRANSPARENT ELECTRODE |
| 3 | METAL OXIDE SEMICONDUCTOR LAYER |
| 4 | SUBSTRATE |
| 5 | ELECTRODE |
| 6 | COUNTER ELECTRODE |
| 7 | ELECTROLYTE LAYER |

The invention claimed is:

1. An electrode for incorporation in a solar cell, the electrode comprising a mixture of carbon carrying a metal and a binder, the carbon having a specific surface area equal to or larger than 100 $m^2/g$, and the metal being either a pure metal or an alloy metal comprising at least one metal selected from the group consisting of Pt, Ru, Co, Ti, Ni, Al and Au, wherein the solar cell exhibits a photoelectric transfer coefficient of about 5.8% or greater.

2. The electrode according to claim 1, which is formed on an electrically conductive substrate.

3. The electrode according to claim 2 wherein the electrically conductive substrate is made of glass, a polymer film or a metal.

4. The electrode according to claim 1 wherein the carbon is needle-like carbon, fullerene, carbon nanotube or electrically conductive carbon black.

5. The electrode according to claim 1 wherein the specific surface area of the carbon is equal to or larger than 300 $m^2/g$.

6. The electrode according to claim 1 wherein the amount of the metal carried by the carbon is equal to or more than 5 weight percent of the carbon.

7. The electrode according to claim 1, wherein the electrode is disposed immediately adjacent to an electrolytic layer.

8. The electrode according to claim 1, wherein the binder is insoluble to electrolytes.

9. An electrode for incorporation in a solar cell, the electrode comprising a mixture of carbon carrying both a metal and a binder, wherein the metal is either a pure metal or an alloy metal comprising at least one metal selected from the group consisting of Pt, Ru, Co, Ti, Ni, Al and Au and the amount of metal in the electrode ranges between 5 wt % and 15 wt % relative to the carbon, wherein the solar cell exhibits a photoelectric transfer coefficient of about 5.8% or greater.

10. The electrode according to claim 1, wherein the binder in the electrode comprises more than 5 wt % of the carbon.

11. The electrode according to claim 1, further comprising an electrolytic layer disposed adjacent to the electrode and a semiconductor layer disposed adjacent to the electrolytic layer, the electrolytic layer having a thickness of between about 1 micron and 100 microns.

* * * * *